(12) United States Patent
Baril

(10) Patent No.: US 11,058,459 B2
(45) Date of Patent: Jul. 13, 2021

(54) TWO-PIECE CUTTING GUARD WITH EVACUATION PORTS

(71) Applicant: Covidien LP, Mansfield, MA (US)

(72) Inventor: Jacob C. Baril, Norwalk, CT (US)

(73) Assignee: Covidien LP, Mansfield, MA (US)

( * ) Notice: Subject to any disclaimer, the term of this patent is extended or adjusted under 35 U.S.C. 154(b) by 46 days.

(21) Appl. No.: 16/711,598

(22) Filed: Dec. 12, 2019

(65) Prior Publication Data

US 2021/0177461 A1 Jun. 17, 2021

(51) Int. Cl.
*A61B 17/34* (2006.01)
*A61B 90/00* (2016.01)
*A61B 17/00* (2006.01)

(52) U.S. Cl.
CPC ...... *A61B 17/3494* (2013.01); *A61B 17/3423* (2013.01); *A61B 2017/00862* (2013.01); *A61B 2090/036* (2016.02); *A61B 2217/005* (2013.01)

(58) Field of Classification Search
CPC .......... A61M 39/06; A61M 2039/0626; A61M 29/00; A61B 17/3494; A61B 2017/00862; A61B 2090/036; A61B 2217/005; A61B 17/3423; A61B 17/0293; A61B 17/0218; A61B 17/3462; A61B 2017/3447; A61B 2017/3464; A61B 2017/3466; A61B 2017/3484; A61B 17/0206; A61B 17/3417; A61B 17/3439; A61B 2017/00265; A61B 2017/00287; A61B 17/3496; A61B 17/3498; A61B 2017/0225; A61B 2017/0287; A61B 2017/320064; A61B 2017/3419; A61B 2017/3427; A61B 2017/3441; A61B 2017/3445; A61B 2017/3449; A61B 2017/349; A61B 2017/3429; A61B 2017/3431; A61B 2017/3488; A61B 17/02; A61B 2017/0212; A61B 1/32; A61B 17/027; A61B 2218/008; A61B 2090/0801; A61B 2090/08021
See application file for complete search history.

(56) References Cited

U.S. PATENT DOCUMENTS 5,578,000 A 11/1996 Greff et al.
5,941,873 A 8/1999 Korenfeld
(Continued)

*Primary Examiner* — Elizabeth Houston
*Assistant Examiner* — Alyssa M Keane
(74) *Attorney, Agent, or Firm* — Carter, DeLuca & Farrell LLP

(57) ABSTRACT

A tissue guard for insertion within an access device disposed within an operating cavity includes a base section defining open proximal and distal ends and a lumen extending therethrough between the open proximal end and the open distal end. The base section includes one or more openings in a side thereof in fluid communication with the lumen. The proximal end of the base section includes an evacuation ring in fluid communication with the lumen. A tissue cuff is configured to encapsulate the base section and is selectively moveable between a distal position for facilitating insertion of the tissue guard within an access device disposed within a tissue opening in an operating cavity and a proximal position wherein the tissue cuff encloses the one or more openings to form an evacuation channel between the one or more openings and the evacuation ring to facilitate fluid evacuation from the operating cavity.

15 Claims, 3 Drawing Sheets

(56) References Cited

U.S. PATENT DOCUMENTS

| | | | |
|---|---|---|---|
| 6,033,362 A | 3/2000 | Cohn | |
| 6,544,210 B1 | 4/2003 | Trudel et al. | |
| 7,789,946 B2 | 9/2010 | Schultz et al. | |
| 7,901,353 B2 | 3/2011 | Vayser et al. | |
| 9,427,288 B1 | 8/2016 | Chenger et al. | |
| 10,076,358 B2 * | 9/2018 | Zergiebel | A61B 17/0218 |
| 2005/0054993 A1 | 3/2005 | Falahee | |
| 2006/0247673 A1 | 11/2006 | Voegele et al. | |
| 2011/0021879 A1 * | 1/2011 | Hart | A61B 17/0293 600/207 |
| 2012/0089093 A1 | 4/2012 | Trusty | |
| 2012/0253134 A1 * | 10/2012 | Smith | A61B 17/0218 600/203 |
| 2012/0289785 A1 * | 11/2012 | Albrecht | A61B 17/0218 600/208 |
| 2013/0184536 A1 | 7/2013 | Shibley et al. | |
| 2014/0330285 A1 | 11/2014 | Rosenblatt et al. | |
| 2016/0158468 A1 | 6/2016 | Tang | |
| 2017/0049427 A1 | 2/2017 | Do et al. | |
| 2017/0325657 A1 | 11/2017 | Prior | |
| 2017/0340866 A1 * | 11/2017 | Richard | A61B 17/3439 |
| 2018/0008250 A1 | 1/2018 | Joseph | |
| 2018/0049771 A1 | 2/2018 | Rhemrev-Pieters | |
| 2020/0367932 A1 * | 11/2020 | Baril | A61B 17/3423 |

* cited by examiner

TWO-PIECE CUTTING GUARD WITH EVACUATION PORTS

FIELD

The present disclosure relates to tissue specimen removal and, more particularly, to tissue guards and systems incorporating the same for use in tissue specimen removal procedures and other surgical procedures.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue guard for insertion within an access device disposed within an operating cavity that includes a base section defining an open proximal end, an open distal end, and a lumen extending through the base section between the open proximal end and the open distal end. The base section includes one or more openings in a side thereof in fluid communication with the lumen. The proximal end of the base section includes an evacuation ring in fluid communication with the lumen. A tissue cuff is configured to encapsulate the base section and is selectively moveable between a distal position for facilitating insertion of the tissue guard within an access device disposed within a tissue opening in the operating cavity and a proximal position wherein the tissue cuff encloses the one or more openings to form an evacuation channel between the one or more openings and the evacuation ring to facilitate fluid evacuation from the operating cavity.

In aspects according to the present disclosure, the distal end of the body section includes a plurality of resilient fins configured to radially move between a narrow insertion configuration to facilitate insertion of the tissue guard within the access device and an expanded configuration to facilitate securing the tissue guard within the access device. In other aspects according to the present disclosure, selective movement of the tissue cuff moves the plurality of resilient fins between the narrow insertion configuration and the expanded configuration.

In aspects according to the present disclosure, the one or more openings is disposed proximate the proximal end of the base section. In other aspects according to the present disclosure, the proximal end of the tissue guard is configured to securely engage a proximal rim of the access device upon insertion thereof. In yet other aspects according to the present disclosure, the evacuation ring includes a connection port adapted to connect to a fluid management system. In still other aspects according to the present disclosure, the connection port is in fluid communication with the evacuation ring.

In aspects according to the present disclosure, the resilient fins are flared to facilitate engagement with the access device. In other aspects according to the present disclosure, the tissue cuff mechanically locks in the proximal position when the resilient fins flare in the expanded configuration.

In accordance with other aspects of the present disclosure, a tissue guard for insertion within an access device disposed within an operating cavity includes a base section defining an open proximal end, an open distal end, and a lumen extending through the base section between the open proximal end and the open distal end. The base section includes a series of openings defined in a side thereof in fluid communication with the lumen and a plurality of resilient fins configured to radially move between a narrow insertion configuration to facilitate insertion of the tissue guard within the access device and an expanded configuration to facilitate securing the tissue guard within the access device. The proximal end includes a connection port adapted to connect to a fluid management system. A tissue cuff is configured to encapsulate the base section and is selectively moveable between a distal position for facilitating insertion of the tissue guard within the access device disposed within a tissue opening in the operating cavity and a proximal position wherein the tissue cuff encloses the series of openings to form evacuation channels between the series of openings and the connection port to facilitate fluid evacuation from the operating cavity.

In aspects according to the present disclosure, selective movement of the tissue cuff moves the plurality of resilient fins between the narrow insertion configuration and the expanded configuration.

In aspects according to the present disclosure, the series of openings is disposed proximate the proximal end of the base section. In other aspects according to the present disclosure, the proximal end of the tissue guard is configured to securely engage a proximal rim of the access device upon insertion thereof. In yet other aspects according to the present disclosure, the resilient fins are flared to facilitate engagement with the access device. In still other aspects according to the present disclosure, the tissue cuff mechanically locks in the proximal position when the resilient fins flare in the expanded configuration.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1A:
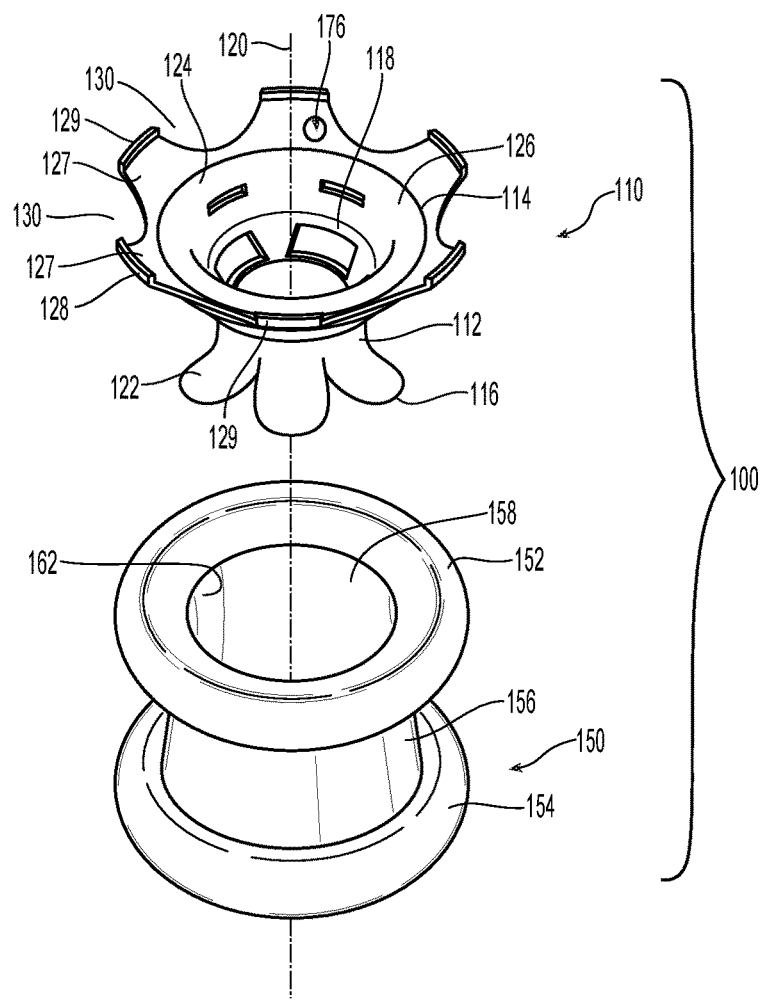
FIG. 1A is an exploded, top, perspective view of a system provided in accordance with the present disclosure including an access device and a tissue guard.
Figure 1B:
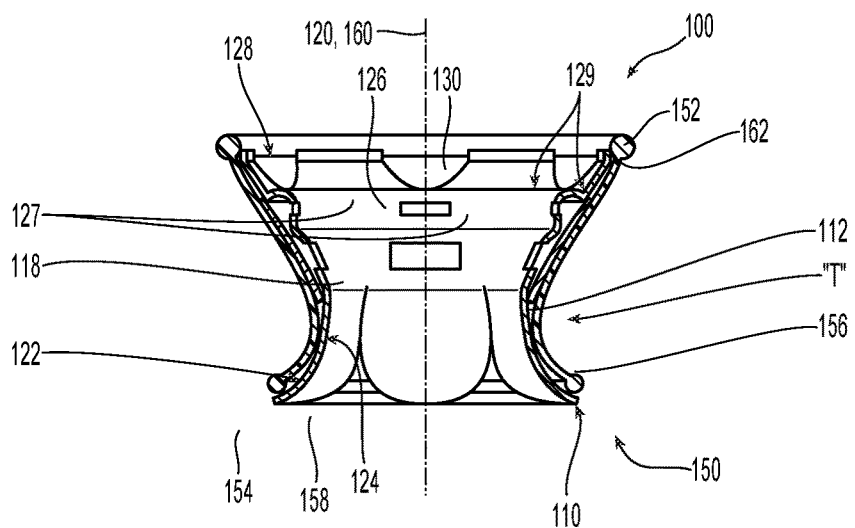
FIG. 1B is a cross-sectional view of the system of FIG. 1A disposed within an opening in tissue.

Turning to FIGS. 1A and 1B, a system 100 provided in accordance with the present disclosure includes a tissue guard 110 and an access device 150. Tissue guard 110 includes a base section 110a and a tissue cuff 110b. Base section 110a is monolithically formed as a single piece of material, e.g., a biocompatible plastic such as, for example, polyethylene, polycarbonate, etc., from any suitable method, e.g., injection molding. Base section 110a includes a proximal or instrument end 114 and a distal or insertion end 116. The material, thickness, and configuration of base section 110a are such that base section 110a defines sufficient stiffness to maintain its shape when positioned within an opening in tissue "T" and/or when engaged within access device 150. However, the material, thickness, and configuration of base section 110a also provides sufficient resilient flexibility to permit manipulation of tissue guard 110 from an at-rest position for insertion into an opening in tissue "T" and/or for engagement within an access device 150, with base section 110a expanding after insertion to an expansion position.

Continuing with reference to FIGS. 1A and 1B, base section 110a includes a body 112 defining the proximal and distal ends 114, 116 and a lumen 118 extending therethrough between open proximal and distal ends 114, 116, respectively. Lumen 118 defines a longitudinal axis 120 and is configured to receive one or more surgical instruments (not shown) therethrough. In embodiments, body 112 defines a funnel-shaped configuration wherein a diameter of body 112 at open proximal end 114 thereof is greater than a diameter of body 112 at open distal end 116 thereof. As explained in detail below, the distal end 116 is transitionable from an insertion configuration to an expanded configuration after insertion. Additionally or alternatively, the exterior surface 122 of body 112 may define a concave configuration while the interior surface 124 of body 112, which defines lumen 118, may define a convex configuration.

Tissue guard 110 further includes a lip 126 extending radially outwardly from open proximal end 114 of body 112 about the annular perimeter thereof. In this manner, lip 126 extends radially outwardly from lumen 118. Lip 126 may extend radially outwardly from body 112 at an oblique angle relative thereto. More specifically, an angle defined between lip 126 and the exterior surface 122 of body 112 may, in embodiments, be from about 90 degrees to about 135 degrees. Lip 126 defines a circumferential outer edge 128. A plurality of spaced-apart cut-outs 130 are defined about the outer circumference of lip 126, thereby interrupting outer edge 128 of lip 126 such that lip 126 defines a plurality of spaced-apart tabs 127 each including an outer edge segment 129 of discontinuous outer edge 128. Cut-outs 130 facilitate flexion of lip 126, e.g., to facilitate insertion into the opening in tissue "T" and/or engagement within access device 150.

Base section 110a of tissue guard 100 includes one or more resilient fins 116a, 116b, 116c disposed at the insertion or distal end 116 thereof that are transitionable between a compressed, at-rest configuration to facilitate insertion of the tissue guard 100 into the access device 150 and the expanded position wherein the resilient fins 116a, 116b, 116c flare to engage the tissue opening "T" within access device 150, e.g., provide an outward force to seat the tissue guard 100 within access device 150 and against the inner periphery of tissue opening "T".

Base section 110a also includes a series of openings 113 defined therein around a periphery thereof configured to facilitate smoke evacuation from the operating cavity. More particularly, the series of openings 113 are disposed proximate the proximal end 114 of the base section 110a.

Figure 2A:
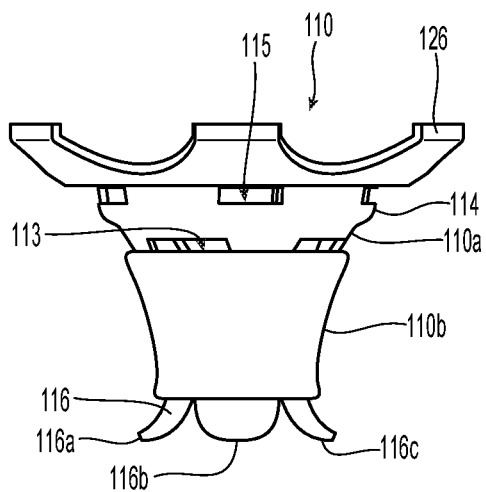
FIG. 2A is a front view of the tissue guard with a distally-oriented tissue cuff poised for insertion within the access device in accordance with the present disclosure.
Figure 2B:
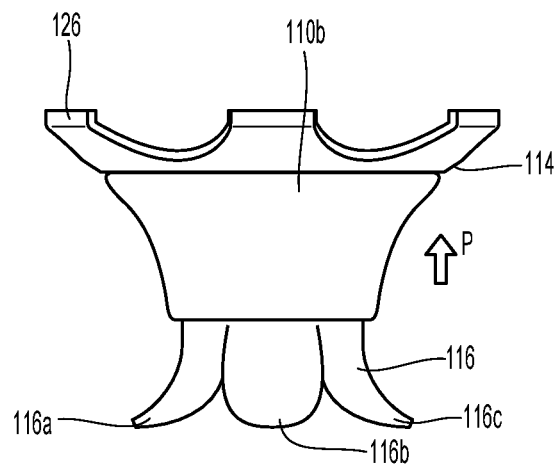
FIG. 2B is a front view of the tissue guard showing proximal movement of the tissue cuff in accordance with the present disclosure.

As mentioned above, tissue guard 110 also includes a tissue cuff 110b that is configured to slidingly engage the distal end 116 of base section 110a. More particularly, tissue cuff 110b is positionable between an insertion configuration (FIG. 2A) and an operational configuration (FIG. 2B). The tissue cuff 110b may come pre-positioned for insertion on base section 110a or the surgeon may engage the tissue cuff 110b over the distal end 116 prior to insertion.

Figure 2C:
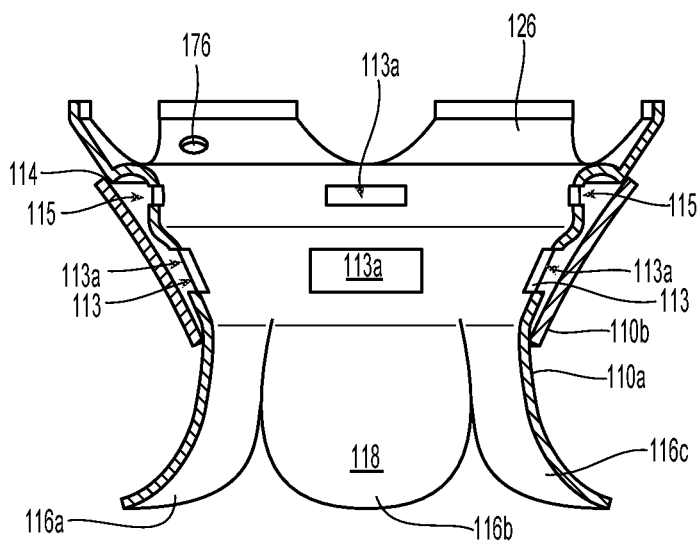
FIG. 2C is a front, perspective view of the tissue guard of FIG. 2 showing the formation of evacuation channels as a result of the proximal movement of the tissue cuff.

As explained above and as best shown in FIGS. 2A-2C, during insertion the tissue cuff 110b is disposed at a distal end 116 of the base section 110a to facilitate insertion. Once inserted, the tissue cuff 110b may be manually slid proximally in the direction "P" to free the resilient fins 116a, 116b, 116c to engage the tissue opening "T" to secure the base section 110a therein. Sliding the tissue cuff 110b further proximally also seats the upper end of tissue cuff 110b against the proximal end 114 of the base section 110a enclosing the series of openings 113 disposed therearound and forming evacuation channels 113a for safely evacuating smoke or fluids from the operating cavity (See FIG. 2C). As can be appreciated, the tissue cuff 113 performs the dual function of compressing the distal resilient fins 116a, 116b, 116c for insertion and enclosing the proximal series of openings 113 to form smoke evacuation channels 113a. The flaring of the resilient fins 116a, 116b, 116c may secure the tissue cuff 110b in the proximal-most position against a proximal rim 152 of the base section 110a.

The material, thickness, and configuration of the base section 110a and tissue cuff 110b of the tissue guard 110 may be selected such that tissue guard 110 is configured to withstand cutting and puncturing by surgical knives, scalpels, pencils, and the like, thereby protecting surrounding tissue "T" and/or access device 150 from being cut or punctured. Tissue guard 110 may additionally or alternatively be configured to inhibit transfer of thermal and/or electrical energy therethrough to protect surrounding tissue "T" and/or access device 150 from thermal and/or electrical energy.

Referring still to FIGS. 1A and 1B, access device 150 may be configured as a tissue retractor, an access port, or other suitable access device configured for positioning within an opening in tissue "T," e.g., a surgical incision or a naturally-occurring orifice, to provide access therethrough into an internal surgical site. Access device 150 includes the proximal rim 152 configured for positioning on an external side of the opening in tissue "T," a distal rim 154 configured for positioning on an internal side of the opening in tissue "T," and a body 156 extending between proximal and distal rims 152, 154, respectively. Body 156 is configured to extend through the opening in tissue "T" and defines a passageway 158 extending longitudinally therethrough to permit access to an internal surgical site through the opening in tissue "T." Passageway 158 defines a longitudinal axis 160. At least a portion of body 156 of access device 150 may be flexible to facilitate insertion and positioning of access device 150 within the opening in tissue "T." In embodiments, body 156 is formed from a flexible sleeve of material including one or more layers of material. Further, access device 150 may be selectively adjustable, e.g., by rolling proximal rim 154 distally about body 156, to retract tissue "T" and/or secure access device 150 within the opening in tissue "T." Access device 150 further defines an inwardly-extending overhang 162 between proximal rim 154 and body 156 and extending annularly about passageway 158.

As shown in FIG. 1B, in use, access device 150 is positioned within an opening in tissue "T" such that, as noted above, distal rim 154 is disposed on an internal surface of tissue "T" on the internal side of the opening in tissue "T," body 156 extends through the opening in tissue "T," and proximal rim 152 is disposed on an exterior surface of tissue "T" on the external side of the opening in tissue "T." As also noted above, access device 150 may be adjusted to conform access device 150 to a patient's anatomy, retracting tissue "T" and/or securing access device 150 within the opening in tissue "T."

With access device 150 disposed within the opening in tissue "T," tissue guard 110, led by open distal end 116 thereof, is inserted into passageway 158. As mentioned above, the tissue cuff 110b compresses the resilient fins 116a, 116b, 116c to facilitate insertion. Tissue guard 110 is configured relative to access device 150 such that an outer diameter of outer edge 128 of lip 126 of tissue guard 110 is greater than an inner diameter of proximal rim 152 of access device 150 such that tissue guard 110 is required to be flexed or otherwise manipulated to permit lip 126 to pass distally through proximal rim 152 into the portion of passageway 158 defined by body 156 of access device 150. More specifically, tissue guard 110 may be flexed or otherwise manipulated such that tabs 127 of lip 126 are urged proximally and inwardly relative to body 112, thus reducing the outer-most diameter of tissue guard 110 to facilitate passage through proximal rim 152 of access device 150. Cut-outs 130, as noted above, facilitate the flexion of lip 126 in this manner to enable passage through proximal rim 152 of access device 150.

Once tissue guard 110 is inserted sufficiently into passageway 158 of access device 150 such that lip 126 is disposed distally of proximal rim 152 of access device 150, tissue guard 110 may be released, allowing tissue guard 110 to return to or towards its at-rest position, whereby tabs 127 of lip 126 and, more specifically, outer edge segments 129 of tabs 127, are engaged with overhang 162, thereby locking tissue guard 110 in engagement within access device 150. In embodiments, tabs 127 of lip 126 may be configured to "snap" into engagement with overhang 162 and, in such embodiments, may produce an audible and/or tactile response that confirms the engagement of tissue guard 110 within access device 150.

With tissue guard 110 engaged within access device 150 and the tabs 127 positioned under lip 126 as detailed above, the tissue cuff 110b may be moved proximally to all expansion of the distal resilient fins 116a, 116b, 116c to engage the base section 100a against tissue opening "T". As mentioned above, movement of the tissue cuff 110b to a proximal-most position seats the tissue cuff 110b atop the proximal end of the base section 110a and encloses the series of openings 113 to form smoke evacuation channels 113a. Smoke evacuation channels 113 communicate with the evacuation ring 115 disposed within the proximal end 114 of tissue guard 110 which, in turn, connects to connection port 176 of a fluid management or smoke evacuation system 700 explained in further detail below. The evacuation ring 115 is configured as a generally hollow sleeve disposed proximate the inner peripheral surface of the proximal end 114 of the tissue guard 110 and is configured to direct evacuation fluids and smoke to the connection port 176 and to the fluid management or smoke evacuation system 700.

With tissue guard 110 engaged within access device 150 as detailed above, surgical instrumentation may be inserted through lumen 118 of tissue guard 110 into the internal surgical site to, for example, extract a tissue specimen therefrom. Tissue guard 110, as noted above, protects tissue "T" as well as access device 150 during the insertion, manipulation, use and withdrawal of any such surgical instrumentation.

Figure 3:
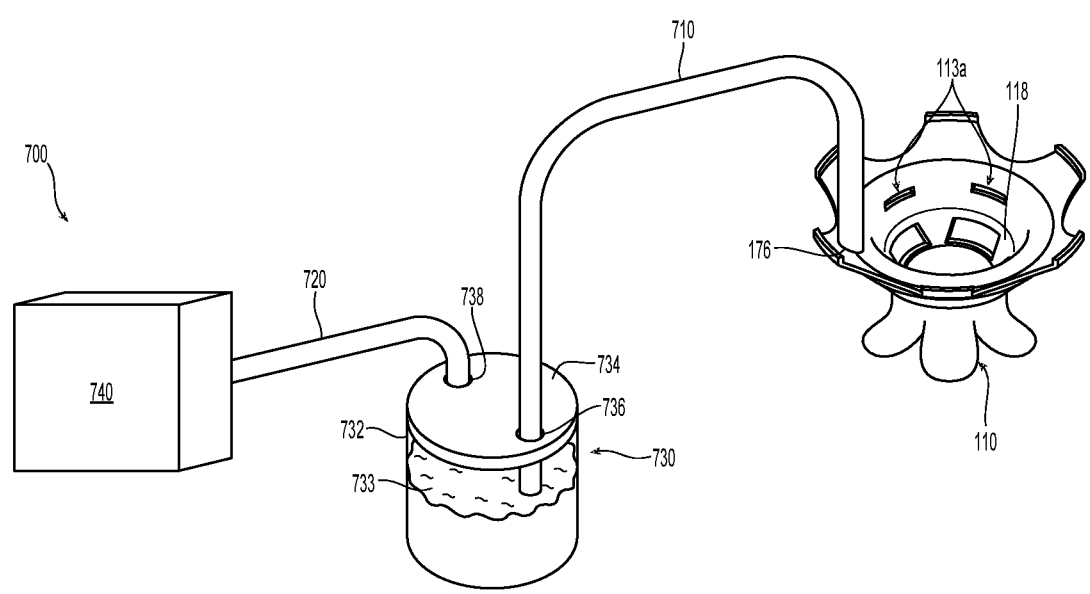
FIG. 3 is a system provided in accordance with the present disclosure including the tissue guard of FIGS. 2A-2C, tubing, a collection reservoir, and a smoke evacuation source.

Turning to FIG. 3, a fluid or smoke evacuation system 700 provided in accordance with the present disclosure is shown generally including tissue guard 110, tubing 710, 720, a collection reservoir 730, and a smoke evacuation (or vacuum) source 740. Tissue guard 110 and tubing 710 are detailed above and are coupled to one another, e.g., via engagement of one end of tubing 710 about connection port 176 of tissue guard 110. The other end of tubing 710 extends into collection reservoir 730 in sealing relation therewith.

Collection reservoir 730 includes a base 732 and a lid 734 sealed about base 732. Lid 734 defines first and second ports 736, 738 configured to receive ends of tubing 710, 720, respectively, in sealing relation therewith. These ends of tubing 710, 720 extend into the interior volume 733 of base 732 and are spaced-apart from one another as well as the bottom of base 732. Tubing 720 extends from collection reservoir 730 to smoke evacuation source 740 wherein the other end of tubing 720 is coupled to smoke evacuation source 740. In this manner, upon activation of smoke evacuation source 740, suction is established through evacuation channels 113a of tissue guard 110, tubing 710, collection reservoir 730, tubing 720, to smoke evacuation source 740.

During use, this suction, in addition to evacuating smoke from lumen 118 of tissue guard 110, may also suction liquids, tissue, and/or debris through tubing 710. However, as a result of the ends of tubing 710, 720 being spaced-apart from one another within collection reservoir 730 and spaced-apart from the bottom of base 732 of collection reservoir 730, the liquids, tissue, and/or debris are suctioned into collection reservoir 730 and deposited therein, while only the smoke and other gaseous fluids are further suctioned from collection reservoir 730 through tubing 720 to smoke evacuation source 740. As such, smoke evacuation source 740 is protected by inhibiting suctioning of liquids, tissue, and/or debris into smoke evacuation source 740.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue guard for insertion within an access device disposed within an operating cavity, comprising:
   a base section defining an open proximal end, an open distal end, and a lumen extending through the base section between the open proximal end and the open distal end, the base section including at least one opening in a side thereof in fluid communication with the lumen, the proximal end of the base section including an evacuation ring in fluid communication with the lumen; and
   a tissue cuff configured to encapsulate the base section, the tissue cuff selectively moveable between a distal position for facilitating insertion of the tissue guard within an access device disposed within a tissue opening in an operating cavity and a proximal position wherein the tissue cuff encloses the at least one opening to form an evacuation channel between the at least one opening and the evacuation ring to facilitate fluid evacuation from the operating cavity.

2. The tissue guard according to claim 1, wherein the distal end of the body section includes a plurality of resilient fins configured to radially move between a narrow insertion configuration to facilitate insertion of the tissue guard within the access device and an expanded configuration to facilitate securing the tissue guard within the access device.

3. The tissue guard according to claim 2, wherein selective movement of the tissue cuff moves the plurality of resilient fins between the narrow insertion configuration and the expanded configuration.

4. The tissue guard according to claim 2, wherein the resilient fins are flared to facilitate engagement with the access device.

5. The tissue guard according to claim 4, wherein the tissue cuff mechanically locks in the proximal position when the resilient fins flare in the expanded configuration.

6. The tissue guard according to claim 1, wherein the at least one opening is disposed proximate the proximal end of the base section.

7. The tissue guard according to claim 1, wherein the proximal end of the tissue guard is configured to securely engage a proximal rim of the access device upon insertion thereof.

8. The tissue guard according to claim 1, wherein the evacuation ring includes a connection port adapted to connect to a fluid management system.

9. The tissue guard according to claim 8, wherein the connection port is in fluid communication with the evacuation ring.

10. A tissue guard for insertion within an access device disposed within an operating cavity, comprising:
    a base section defining an open proximal end, an open distal end, and a lumen extending through the base section between the open proximal end and the open distal end, the base section including a series of openings defined in a side thereof in fluid communication with the lumen and a plurality of resilient fins configured to radially move between a narrow insertion configuration to facilitate insertion of the tissue guard within the access device and an expanded configuration to facilitate securing the tissue guard within the access device, the proximal end including a connection port adapted to connect to a fluid management system; and
    a tissue cuff configured to encapsulate the base section, the tissue cuff selectively moveable between a distal position for facilitating insertion of the tissue guard within the access device disposed within a tissue opening in an operating cavity and a proximal position wherein the tissue cuff encloses the series of openings to form evacuation channels between the series of openings and the connection port to facilitate fluid evacuation from the operating cavity.

11. The tissue guard according to claim 10, wherein selective movement of the tissue cuff moves the plurality of resilient fins between the narrow insertion configuration and the expanded configuration.

12. The tissue guard according to claim 10, wherein the series of openings is disposed proximate the proximal end of the base section.

13. The tissue guard according to claim 10, wherein the proximal end of the tissue guard is configured to securely engage a proximal rim of the access device upon insertion thereof.

14. The tissue guard according to claim 10, wherein the resilient fins are flared to facilitate engagement with the access device.

15. The tissue guard according to claim 14, wherein the tissue cuff mechanically locks in the proximal position when the resilient fins flare in the expanded configuration.

* * * * *